United States Patent [19]
Watanabe et al.

[11] 4,271,310
[45] Jun. 2, 1981

[54] METHOD OF DETERMINING CHOLINESTERASE ACTIVITY AND CHOLINE DERIVATIVES FOR USE IN THE METHOD

[75] Inventors: Katsuyuki Watanabe, Tokyo; Tadatoshi Hayashi, Machida, both of Japan; Hiroaki Hayashi, deceased, late of Saitama, Japan; by Atsuko Hayashi, heir; by Yuko Hayashi, heir, both of Wako, Japan; Toshio Tatano, Numazu; Yoshiaki Shmizu, Shizuoka, both of Japan

[73] Assignee: Kyowa Hakko Kogyo Kabushiki Kaisha, Tokyo, Japan

[21] Appl. No.: 29,517

[22] Filed: Apr. 12, 1979

[30] Foreign Application Priority Data

Apr. 17, 1978 [JP] Japan ............................ 53-44122
Apr. 17, 1978 [JP] Japan ............................ 53-45097

[51] Int. Cl.$^3$ .................. C07C 69/88; C07C 69/76
[52] U.S. Cl. ............................ 560/71; 560/55; 560/67; 560/74; 560/103; 560/104; 560/105; 560/110; 424/309
[58] Field of Search ............ 560/110, 105, 104, 103, 560/74, 55, 71, 67; 424/309

[56] References Cited
U.S. PATENT DOCUMENTS
3,998,815  12/1976  Bodor .................................. 560/104

Primary Examiner—Paul J. Killos
Attorney, Agent, or Firm—Wolder, Gross & Yavner

[57] ABSTRACT

Cholinesterase activity is determined by means of the choline and/or acid obtained by the action of cholinesterase on a compound of the formula:

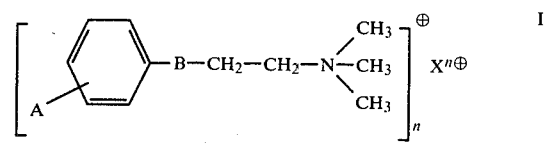

[wherein A represents a hydrogen atom or a $C_{1-5}$ alkyl or alkoxy group and B represents a group of the formula —R-COO— (in which —R— represents an alkenyl group with 2 to 6 carbon atoms); or A represents a hydroxy group in either or both o-positions of the benzene ring or a $C_{1-5}$ alkyl group and B represents a group of the formula —COO—; X represents a stabilizing anion and n represents the charge on the anion]. The method of the invention ensures a high resistance to saturation, good stability of the compounds used as substrates, a conveniently low reaction rate and a high degree of accuracy.

Certain of the compounds of formula I as defined above are novel compounds which are claimed per se.

Examples of the method of the present invention are given and the preparation of the novel compounds is described and exemplified.

21 Claims, No Drawings

METHOD OF DETERMINING CHOLINESTERASE ACTIVITY AND CHOLINE DERIVATIVES FOR USE IN THE METHOD

The present invention relates to a method of determining cholinesterase activity and choline derivatives for use in the method.

Various methods for determining the activity of cholinesterase are known, and all of these known methods use choline derivatives as a substrate for reaction with cholinesterase. It is also known that choline and an acid derived from the choline derivative are formed by the action of cholinesterase on the substrate, which appears to effect hydrolysis.

According to known methods, for example, acetyl choline, butyryl choline, acetyl thiocholine, propyl thiocholine, o-nitrophenyl butyrate or indophenyl acetate may be used as substrates, and buffer solutions containing such substrates at a given concentration may be used for reaction with cholinesterase. Reaction with cholinesterase results in the formation of an acid which causes the pH of the buffer solution to be lowered. Cholinesterase activity is determined with reference to the variation of pH ($\Delta$pH) over a given time [Glass electrode method, Baum G.: Clin. Chimica Acta, 36, 405 (1972)]. However, such choline derivatives possess poor stability and it is thus difficult to conduct the necessary measurements accurately and accordingly it is also difficult to determine the activity of cholinesterase with good results.

It is also known to use benzoyl choline as the substrate (Kalow method) [Kalow W., Genest. K.: Canad. J. Biochem. Physiol. 35, 341 (1957)]. This method includes (i) a process for determining cholinesterase activity by reference to the benzoic acid which is formed when the benzoyl choline used as substrate is decomposed by the action of cholinesterase and (ii) a process for determining cholinesterase activity by reference to the choline which is formed, the amount of choline formed being estimated by the use of choline oxidase which is added to the reaction system (Japanese Patent Application as laid open to public inspection No. 140,984/77 of Kokai Koho). It is, however, difficult to carry out the determination accurately by such processes as a result of the poor stability of the benzoyl choline used as substrate.

Moreover, the determination of cholinesterase activity in blood presents some special difficulties. For example, when the concentration of benzoyl choline used as substrate is too low, the hydrolyzing action of cholinesterase on the substrate proceeds very quickly so that it is very difficult to trace this reaction exactly by manual or mechanical operation. It is thus difficult to determine the amount of cholinesterase present with any degree of accuracy. Moreover, when choline oxidase is used to estimate the choline produced by the action of cholinesterase, the presence of a certain amount of oxygen dissolved in the reaction system is necessary in addition to the formed choline and choline oxidase, but the amount of such oxygen present is usually very low. Furthermore, in such cases, it is not only difficult but also impracticable to enhance the amount of oxygen, for example, by introducing, e.g. blowing, air or oxygen into the reaction system. On the other hand, choline is liberated very quickly by the action of cholinesterase on benzoyl choline used as the substrate and is converted into betaine aldehyde in the presence of oxygen by the action of choline oxidase. As a result, an equimolar amount of hydrogen peroxide is formed which is introduced into a colour-developing solution to determine the amount of choline formed as a result of the cholinesterase activity. These reactions are, however, discontinued as a result of the consumption of oxygen in the reaction system. It is thus difficult to accurately determine the amount of choline formed.

It is thus necessary to perform the measurement over the shortest possible time, before the consumption of the oxygen dissolved in the reaction solution, when benzoyl choline is used as the substrate.

On the other hand, when the concentration of benzoyl choline is too high, it is difficult to determine exactly the amount of cholinesterase as benzoyl choline per se serves to inhibit the cholinesterase in blood and the reaction is discontinued.

It is also known to determine cholinesterase activity by using butyl thiocholine as the substrate [Szasz, G.: Clin. Chim. Acta, 19, 191 (1968)]. The cholinesterase activity is determined by forming thiocholine as a reaction product from butyl thiocholine and cholinesterase, subjecting the thiocholine formed to reaction with a compound relating to 5,5'-dithiobisbenzoic acid (e.g. 2,2'- or 4,4'-dithiopyridine) to obtain a coloured substance, and measuring the extinction coefficient of this substance. However, both butyl thiocholine and 5,5'-dithiobisbenzoic acid and related substances used for this process are very unstable and undergo natural oxidation. Also, the reaction performed by this process is the same as the reaction of various thiol derivatives in blood (e.g. glutathione) so that again it is not possible to make any measurement with accuracy.

In order to overcome, at least in part, the various disadvantages of the known processes, we have discovered a new method for determining cholinesterase activity which comprises the use of compounds, as substrates, which exhibit good stability and also decompose by the action of cholinesterase at a conveniently slow reaction rate.

In addition to the above, the new method ensures a high resistance to saturation. Saturation is a difficulty which is described hereinafter and which gives rise to inaccurate results. Our invention thus provides a method which overcomes, at least in part, the disadvantages of known methods for determining cholinesterase activity and provides results having improved accuracy.

Thus according to one feature of the present invention there is provided a method of determining cholinesterase activity which comprises reacting cholinesterase with a compound of the formula:

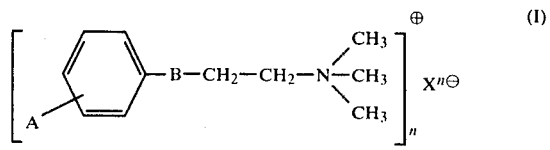

[wherein A represents a hydrogen atom or a $C_{1-5}$ alkyl or alkoxy group and B represents a group of the formula: —R—COO— (in which —R— represents an alkenyl group with 2 to 6 carbon atoms); or A represents a hydroxy group in either or both o-positions of the benzene ring or a $C_{1-5}$ alkyl group and B represents a group of the formula —COO—; X represents a stabilising anion and n represents the charge on the anion]

and determining the cholinesterase activity by means of the choline and/or acid thereby obtained.

The method of the present invention is preferably effected using a compound of formula I wherein X represents a water solubilising stabilising anion, e.g. a halide ion and n is 1, especially a chloride ion.

The method of the present invention may also, for example, be effected by the use of a compound of formula I in which A represents a hydrogen atom or a methyl or methoxy group in the p-position of the benzene ring and B represents a group of the formula —R—COO— (wherein R represents an alkenyl group with 2 to 6 carbon atoms) or A represents a methyl group in either or both o-positions of the benzene ring and B represents the group —COO—.

variation of pH of a solution containing the formed acid.

It is possible to determine the amount of choline formed, for example, by subjecting the choline to the action of choline dehydrogenase in the presence of NAD and feeding the same into a colour-developing solution. It is also possible to subject the formed choline to the action of choline oxidase to produce hydrogen peroxide which is then added to a colour-developing solution. Various known methods (e.g. the method proposed by Kalow et al and the method proposed by Takahashi et al) may be used to determine the variation of pH caused by the acid formed.

Preferred compounds of formula (I) are listed below together with their physical properties in Table 1,

TABLE 1

| Structural formula | Name | M.P. |
|---|---|---|
| [H₃C—⟨⟩—CH=CH—C(=O)—O—CH₂—CH₂—N⁺(CH₃)₃] Cl⁻ | p-methylcinnamoyl choline chloride (Compound No. I) | 170–174° C. |
| [H₃CO—⟨⟩—CH=CH—C(=O)—O—CH₂—CH₂—N⁺(CH₃)₃] Cl⁻ | p-methoxycinnamoyl choline chloride (Compound No. II) | 183–184° C. |
| [o-CH₃-C₆H₄—C(=O)—O—CH₂—CH₂—N⁺(CH₃)₃] Cl⁻ | o-methylbenzoyl choline chloride (Compound No. III) | 142–143° C. |
| [⟨⟩—CH=CH—C(=O)—O—CH₂—CH₂—N⁺(CH₃)₃] Cl⁻ | Cinnamoylcholine chloride (Compound No. IV) | 196–197° C. |
| [m-CH₃-C₆H₄—C(=O)—O—CH₂—CH₂—N⁺(CH₃)₃] Cl⁻ | m-methylbenzoyl choline chloride (Compound No. V) | |
| [o-OH-C₆H₄—C(=O)—O—CH₂—CH₂—N⁺(CH₃)₃] Cl⁻ | o-hydroxy benzoyl choline chloride (Compound No. VI) | |

| Compound | N.M.R. (in CD₃OD) | IR(KBr) cm⁻¹ |
|---|---|---|
| I | 2.00 s 3H; 3.58 s 9H; 3.78 m 2H; 4.68 m 2H; 6.48 d = 18Hz1H; 7.18 d = 8Hz2H; 7.50 d = 8Hz2H; 7.72 d = 18Hz1H | 1711; 1625; |
| II | 3.30 s 9H; 3.83 s 3H; 3.87 m 2H; 4.68 m 2H; 6.42 d = 18Hz1H; 6.93 d = 10Hz2H; .758 d = 10Hz2H; 7.72 d = 18Hz1H | 1710; 1640; 1605, 1175; 825; 805 |
| III | 2.60 s 3H; 3.33 s 9H; 3.93 m 2H; 4.81 s 2H; 7.32 m 3H; .795 m 1H | 1730; 742 |
| IV | 3.35 s 9H; 3.95 m 2H; 4.75 m 2H; 7.18 d = 8Hz 2H; 7.22 d = 8H 2H; 7.60 m 5H | 1720; 1635; 775 |

Thus according to the method of the present invention, a compound of formula (I) as hereinbefore defined is used as substrate and is subjected to reaction with cholinesterase to form choline and/or an acid. Cholinesterase activity is determined for example, by measuring the choline and/or acid formed, although it is possible to determine cholinesterase activity by referring to the In Table 1, Compounds I, II and IV are new compounds, although the compounds represented by the formula:

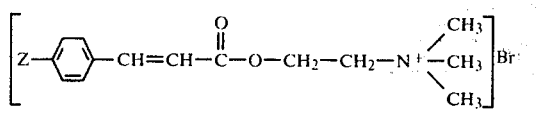

(IIa)

(wherein Z represents —NO₂ or

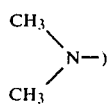

have been reported in Chemical Abstracts, 58, 5940h which describes the compounds of formula (IIa) as exhibiting cholinesterase inhibiting activity, but does not disclose the use of these compounds as substrates for use in determining cholinesterase activity.

The compound of formula III is a new compound but the compound of formula V is old [Chemical Abstracts, 72, 53978t]. This prior art literature describes a compound analogous to the compound of formula III having an o-nitro group in place of an o-methyl group, as well as a compound analagous to the compound of formula V having a m-chloro group in place of a m-methyl group, and teaches that such compounds are active inhibitors of plant growth. The use of such compounds as substrates in determining cholinesterase activity is not however taught or suggested by this prior art literature.

The compound of formula VI is old, being described in Hoppe-Seyler's Zeitschrift für Physiologische Chemie, Berlin, 288, 51 (1951) which is however silent on the use of this compound as a substrate in determining cholinesterase activity.

The process for determining cholinesterase activity by using a compound of formula I as hereinbefore defined as substrate is preferably effected, for example, by subjecting choline which has been formed by the action of cholinesterase, to the action of choline oxidase to form hydrogen peroxide and introducing the same into a colour-developing system (hereinafter referred to as Method A) or by measuring the lowering of pH caused by the acid, which is formed by the action of cholinesterase, by means of an electrode or a pH-indicating agent (hereinafter referred to as Method B).

Method A may be carried out, for example, in the following manner.

The desired amount of an appropriate colour-developing reagent (for example, 4-aminoantipyrine, phenol etc.), choline oxidase (prepared, for example, according to Japanese Patent Application as laid open to public inspection No. 130,984/77 or according to Reference appearing hereinafter), a peroxidase and a substrate of the present invention is added to an appropriate buffer solution [for example, a 0.002-0.1 M tris HCl buffer solution (pH 7.0-8.0)]. The solution thus-prepared is placed in contact with a test sample (cholinesterase or a cholinesterase-containing material such as for example, blood, serum and diluted blood or serum) to carry out the reaction. The substrate is decomposed by the action of cholinesterase to produce choline which is then decomposed into betaine aldehyde and hydrogen peroxide by the action of choline oxidase. The hydrogen peroxide thus-formed is reacted with phenol and 4-aminoantipyrine in the presence of a peroxidase, resulting in a quinoneimine-type pigment. The amount of the pigment formed is determined by measuring its optical density (hereinafter referred to as OD), which corresponds to the activity of cholinesterase.

The reaction is preferably effected at 20°–40° C. for one minute to one hour.

Method B is exemplified as follows.

This method is conveniently carried out in a similar manner to the Shibata-Takahashi Method, reported by G. Kitamura ["Jissen Rinsho Kagaku", page 364, published by Ishika Shuppansha, Japan] by reference to the OD of phenol red in various buffer solutions having different pHs. In order to determine cholinesterase activity, the variation of pH caused by an acid formed by the action of cholinesterase is indirectly determined by measuring the variation of OD of phenol red in the reaction solution.

Table 2 indicates the reaction rates of the compounds of formula I which may be used for the process of the present invention. The reaction rate is indicated by reference to the reaction rate of benzoyl choline which is a known substrate. The reaction rate was determined in the following manner.

Each (0.2 mg) of the substrates shown in Table 2 was added to a tris HCl buffer solution (3 ml; pH 7.5) containing the following ingredients:

| | |
|---|---|
| 4-Aminoantipyrine | 3 mg |
| Phenol | 2.8 mg |
| Choline oxidase (prepared in Reference 2) | 7.05 Unit |
| Peroxidase (Worthington Corpn., U.S.A.) | 9.1 Unit |

Each solution was preliminarily heated at 37° C. for 10 minutes and a standard serum (each 20 μl) was added thereto. The variation of OD was then measured continuously to determine the rate of increase in OD in a unit of time (min). In Table 2, the rate of increase of OD of benzoyl choline in a unit of time is referred to as 1.

TABLE 2

| Compound No. | Name | In Formula (I) A | B | Reaction rate |
|---|---|---|---|---|
| 7 | Benzoyl choline chloride | ⌬— | O‖ —C—O— | 1 |
| 1 | p-methylcinnamoyl choline chloride | CH₃—⌬— | O‖ —CH=CH—C—O— | 0.043–0.050 |
| 2 | p-methoxycinnamoyl choline chloride | H₃CO—⌬— | O‖ —CH=CH—C—O— | 0.017–0.019 |
| 3 | o-methylbenzoyl choline chloride | ⌬(CH₃)— | O‖ —C—O— | 0.32–0.37 |

TABLE 2-continued

| Compound | | In Formula (I) | | Reaction rate |
|---|---|---|---|---|
| No. | Name | A | B | |
| 4 | Cinnamoyl choline chloride | ⟨phenyl⟩— | —CH=CH—C(=O)—O— | 0.06–0.07 |
| 5 | m-methylbenzoyl choline chloride | CH₃-⟨phenyl⟩— | —C(=O)—O— | 0.70–0.80 |
| 6 | o-hydroxybenzoyl choline chloride | OH-⟨phenyl⟩— | —C(=O)—O— | 0.06–0.07 |

Note:
Compound No. 7 reference compound
Nos. 1–4 new compounds of the invention
5–6 old compounds of the invention The solution stabilities of the compounds (substrates) of the present invention as well as the solution stabilities of the known substrates were determined and shown in Table 3, in which the decomposition rate of benzoyl choline is referred to as 1. The decomposition rate was determined in the following manner.

A tris HCl buffer solution (0.05 M; pH 7.5) containing a specified compound of formula I (0.615 millimol/3 ml) was prepared and allowed to stand at 37° C. for 3 days. After this, the decomposition rate was determined on the basis of the amount of choline produced from this compound. In a similar manner to that described above, hydrogen peroxide which had been produced by the action of choline oxidase was treated with 4-aminoantipyrine to form a quinoneimine-type pigment, and its OD at 500 nm was measured to determine the amount of choline formed. The amount of this pigment depends upon the amount of choline produced so that a smaller amount of the pigment formed indicates a lower decomposition rate.

As is apparent from Table 3, the known substrates such as benzoyl choline and acetyl choline are liable to decompose relatively rapidly with time, and their blank values are also liable to increase over a period of time after the preparation of reagents containing such substrates. On the other hand, the substrates of the present invention decompose slowly and have better preservability and such properties are clearly advantageous for the determination of cholinesterase activity.

TABLE 3

| Compound | | Structural formula (I) | | Decomposition rate |
|---|---|---|---|---|
| No. | Name | A | B | |
| 7 | Benzoyl choline chloride | ⟨phenyl⟩— | —C(=O)—O— | 1 |
| 8 | Acetyl choline chloride | CH₃— | —C(=O)—O— | 2 |
| 9 | Propionyl choline chloride | CH₃—CH₃— | —C(=O)—O— | 2.3 |
| 1 | p-methylcinnamoyl choline chloride | CH₃-⟨phenyl⟩— | —CH=CH—C(=O)—O— | 0.1 |
| 2 | p-methoxycinnamoyl choline chloride | HCO-⟨phenyl⟩— | —CH=CH—C(=O)—O— | 0.05 |
| 3 | o-methylbenzoyl choline chloride | CH₃-⟨phenyl⟩— | —C(=O)—O— | 0.002 |
| 4 | Cinnamoyl choline chloride | ⟨phenyl⟩— | —CH=CH—C(=O)—O— | 0.26 |
| 5 | m-methylbenzoyl choline chloride | CH₃-⟨phenyl⟩— | —C(=O)—O— | 0.005 |
| 6 | o-hydroxybenzoyl choline chloride | OH-⟨phenyl⟩— | —C(=O)—O— | 0.5 |

Note:
Nos. 1–4 new compounds
5–6 old compounds
1–6 compounds of the invention
7–9 comparative compounds According to another feature of the present invention, there are provided compounds of formula I wherein A represents a hydrogen atom or a methyl or methoxy group in the para-position of the benzene ring and B represents a group of the formula —R—COO— (wherein —R— represents an alkenyl group with 2 to 6 carbon atoms); or A represents a methyl group in either or both ortho-positions of the benzene ring and B represents a group of the formula —COO—; X represents a stabilising anion and n represents the charge on the ion.

The compounds of formula I in which X represents a halide ion, e.g. a chloride ion, and n is 1 are preferred, by virtue of their use as substrates in determining cholinesterase activity.

Especially preferred compounds of the present invention by virtue of their use as substrates in determining cholinesterase activity include:

p-methylcinnamoyl choline chloride,
p-methoxycinnamoyl choline chloride,
o-methylbenzoyl choline chloride, and cinnamoyl choline chloride.

These new derivatives may be produced in a similar manner to that applicable to the production of known choline derivatives, for example by using an acid derivative and a halogenated choline.

The reaction between the acid derivative and the halogenated choline may, for example, be effected in the absence of a solvent, in which case the reaction is preferably effected at a temperature of from 100°–200° C., conveniently for 2–8 hours. When the reaction is effected in the presence of an appropriate solvent such as for example chloroform, toluene, benzene and the like, the reaction is preferably effected at a temperature of from 20°–60° C., conveniently for 8–20 hours. Isolation and purification of the desired compound may for example be effected in the usual manner applicable to the synthesis of organic compounds.

According to a further feature of the present invention there are provided compounds of formula I [wherein A represents a hydrogen atom or a $C_{1-5}$ alkyl or alkoxy group and B represents a group of the formula —R—COO— (in which —R— represents an alkenyl group with 2 to 6 carbon atoms); or A represents a hydroxy group in either or both o-positions of the benzene ring or a $C_{1-5}$ alkyl group and B represents a group of the formula —COO—; X represents a stabilising anion and n represents the charge on the anion] for use in the method of the present invention.

m-Methylbenzoyl choline chloride and o-hydroxybenzoyl choline chloride are preferred compounds for use in the method of the present invention.

The present invention also provides a reagent for determining cholinesterase activity which comprises in combination a compound of formula I (as hereinbefore defined), a colour-developing reagent, choline oxidase and a peroxidase. The colour-developing reagent preferably comprises 4-aminoantipyrine and phenol.

EXAMPLE 1

Determination of cholinesterase activity by using a substrate of the present invention and choline oxidase:

(A) Preparation of reagent:

In conventional manner, a reagent is prepared by using a 0.05 M tris-HCl buffer solution (pH 7.5) containing the following ingredients:

| | |
|---|---|
| 4-Aminoantipyrine | 3 mg |
| Phenol | 2.8 mg |
| Choline oxidase prepared in Reference 2 | 7.05 U |
| Peroxidase (commercial product of Worthington Biochemical Corpn., U.S.A.) | 9.1 U |
| Substrate (0-methylbenzoyl choline chloride) | 0.2 mg |

(B) Analysis procedure:

Each of the test serums and Q-PAKI standard serum having a cholinesterase activity of 1458 mU/ml (commercial product of Highland Div. Travenol Laboratories Inc., U.S.A.) is added to the thus-prepared reagent (3 ml) and incubated at 37° C. for a pre-determined time (cf. Table 4). The reaction is discontinued by addition of neostigmine (2 mg). Table 4 indicates various optical densities measured at 500 nm by using a spectrometer. For comparison, the substrate according to the present invention is replaced by benzoyl choline, which is a known substrate, to obtain the corresponding values which are also indicated in this table. The reagent containing benzoyl choline is prepared in conventional manner by using 3 ml of a 0.05 M tris-HCl buffer solution (pH 7.5) containing the following ingredients:

| | |
|---|---|
| 4-Aminoantipyrine | 0.5 mg |
| Phenol | 1.4 mg |
| Choline oxidase | 7.15 Unit |
| Peroxidase | 10.3 Unit |
| Substrate (benzoyl choline) | 0.5 mg |

TABLE 4

| Serum used | Substrate used | Optical density after (min)* | | | |
|---|---|---|---|---|---|
| | | 4 | 10 | 20 | 40 |
| Q-PAKI Standard Serum (cholinesterase activity: 1458 mU/ml | III** | 0.140 | 0.350 | 0.700 | 1.400 |
| | VII*** | 0.440 | 1.100 | 1.600 | 1.650 |
| Serum of patient (1) in a case of liver disease | III | 0.081 | 0.202 | 0.404 | 0.808 |
| | VII | 0.255 | 0.638 | 1.300 | 1.650 |
| Serum of patient (2) in a case of kidney disease | III | 0.217 | 0.543 | 1.085 | 2.100 |
| | VII | 0.679 | 1.600 | 1.650 | 1.670 |

Notes:-
*Reaction time
**Ortho-methylbenzoyl choline chloride (Compound III)
***Benzoyl choline chloride (Compound VII)

Where o-methylbenzoyl choline chloride is used, the cholinesterase activity (about 841 mU/ml) of the serum of patient (1) was determined by the following proportional distribution method (hereinafter, the optical density is referred to as OD).

Cholinesterase activity=[1458/(OD of the standard serum)]×[OD of the serum of patient (1)]

Where benzoyl choline chloride is used as the substrate, the cholinesterase activity (about 844 mU/ml) of the serum of patient (1) was similarly determined by the proportional distribution method, with reference to the values measured after 4 and 10 minutes (the values measured after 20 and 40 minutes are likely to be incorrect).

Where o-methylbenzoyl choline chloride is used as the substrate, a similar procedure to the above-mentioned gave an activity of 2260 mU/ml in respect of the serum of patient (2). Where benzoyl choline chloride is used as the substrate, an activity of 2250 mU/ml in respect of the serum of patient 2 is similarly obtained, with reference only to the O.D. (optical density) measured after 4 minutes. This result is believed to be reliable. However, other OD values are likely to be unreliable owing to their saturation. In our view, such saturation may be caused by the lack of sufficient dissolved oxygen which is required by the choline oxidase. In such cases the reaction of benzoyl choline proceeds at an excessively rapid rate. It is desirable in such cases to dilute the serum in order to obtain a reliable result (however, such dilution procedure is virtually impracticable).

Also, from practical viewpoint, the discontinuation of the measurement after 4 minutes can give rise to various disadvantages such as a large error variance.

When the substrates of the present invention are used, however, it is possible to obtain a reliable OD result, without saturation, even when the cholinesterase activity is very high and the reaction is carried out over a long period of time. Thus the substrates of the present invention are very useful for determining cholinesterase activity.

The following table shows the preferred concentrations of the ingredients of the reagent according to the present invention and of the known reagent containing benzoyl choline.

TABLE 5

| Ingredients | A. Reagent of the present invention | B. Reagent of the known type |
|---|---|---|
| 4-Aminoantipyrine | 1–6 mg | 0.1–1 mg |
| Phenol | 0.7–14 mg | 0.7–3 mg |
| Choline oxidase | 1.4–30 Unit | 0.5–10 Unit |
| Peroxidase | 0.1–20 Unit | 0.5–50 Unit |
| Substrate of the present invention | 0.1–6 mg | — |
| Substrate (benzoyl choline) | — | 0.1–1 mg |

Reaction temperature: 20–40° C.
Reaction time: one minute - one hour

As apparent from Table 5, the range of the concentration of benzoyl choline is narrower than the corresponding range of the substrate of the present invention, and thus the versatility of the former is narrower than that of the latter.

EXAMPLE 2

OD values of the standard serum and of the serum of patient (1) (in the case of liver disease) shown in Table 6 were obtained in a similar manner to that described in Example 1 with the exception that o-methylbenzoyl choline was replaced by the other substrates of the present invention detailed in the Table.

It is apparent from these results that the OD values determined are reliable and free from the saturation difficulties referred to above when measured using the substrates of the present invention.

TABLE 6

| Serum used | Substrate Compound No. | OD measured after -minutes* (*reaction time) | | | |
|---|---|---|---|---|---|
| | | 4 | 10 | 20 | 40 |
| Q-PAKI Standard serum (choline) esterase activity: 1458 mU/ml | I | 0.022 | 0.055 | 0.110 | 0.220 |
| | II | 0.008 | 0.021 | 0.042 | 0.084 |
| | IV | 0.031 | 0.079 | 0.158 | 0.316 |
| | V | 0.308 | 0.770 | 1.540 | 3.080 |
| | VI | 0.031 | 0.082 | 0.163 | 0.321 |
| Serum of patient (1) in a case of liver disease | I | 0.012 | 0.032 | 0.063 | 0.126 |
| | II | 0.005 | 0.012 | 0.025 | 0.050 |
| | IV | 0.017 | 0.046 | 0.090 | 0.181 |
| | V | 0.179 | 0.446 | 0.892 | 1.785 |
| | VI | 0.017 | 0.042 | 0.088 | 0.176 |

Notes:
Compound I - p-methylcinnamoyl choline chloride
II - p-methoxycinnamoyl choline chloride
IV - Cinnamoyl choline chloride
V - m-methylbenzoyl choline chloride
VI - o-hydroxybenzoyl choline chloride

EXAMPLE 3

Determination of cholinesterase activity using the substrate of the present invention (in a similar manner to the Shibata-Takahashi Method)

1. Preparation of reagents:

(1) Veronal/$\beta$-glycerophosphoric acid buffer solution (pH 8.3):

5,5-Diethylbarbituric acid (sodium salt; 3.00 g) is dissolved in water (about 500 ml). The solution is treated with 5,5-diethylbarbituric acid (1.00 g) which is dissolved at an elevated temperature. The solution is cooled and is treated with $\beta$-glycerophosphoric acid (sodium salt; 5.00 g), followed by addition of water to make up to 1,000 ml.

(2) Substrate solution (A) Acetyl choline chloride (1 g) is added to water (10 ml) and dissolved.

(B) o-methylbenzoyl choline chloride (0.5 g) is added to water (10 ml) and dissolved.

(3) Phenol red solution:

Phenol red (100 mg) is added to a 0.1 N sodium hydroxide solution (3.0 ml) and water (7.5 ml). The solution is heated to about 60° C. to dissolve the additives completely. The solution is cooled and is made up with water to 250 ml.

(4) Eserine solution:

Physostigmine salicylate (0.1 g) is dissolved in water which is then made up to 100 ml.

(5) Phosphate buffer solution (1/15 M):

(A) Potassium dihydrogen phosphate ($KH_2PO_4$ ... 9.08 g) is dissolved in water which is then made up to 1,000 ml.

(B) Sodium hydrogen phosphate ($NaHPO_4.2H_2O$ ... 11.88 g) is dissolved in water which is then made up to 1,000 ml.

2. Preparation of reaction solution:

| | |
|---|---|
| (1) Veronal/$\beta$-glycerophosphate buffer solution | 1.5 ml |
| (2) Substrate solution | 0.25 ml |
| (3) Phenol red solution | 0.1 ml |
| (4) water | 3.05 ml |

The reaction solution contains the above-mentioned ingredients. The ratio is indicated by volume.

3. Preparation of calibration curve:

Various buffer solutions (potassium dihydrogen phosphate and sodium hydrogen phosphate) are prepared and adjusted in series to different pHs within the range 5.9–8.3. Each (5.0 ml) of the buffer solutions thus-prepared is added to the phenol red solution (0.1 ml) and thoroughly mixed. Each mixture is then kept at 20°±1° C. and OD at 570 nm is measured with reference to water which is used for control purposes. The thus-measured OD and the indicated pH are plotted to obtain a pH-OD calibration curve.

4. Operation for determination:

Vessels for blank test and test sample (serum) receive the reaction solution (each 4.9 ml) and are then preliminarily kept at 37° C. for 5 minutes. After this, water (0.1 ml) and serum (0.1 ml) are added to the vessels for blank test and serum with agitation, followed by carrying out the reaction at 37° C. for 60 minutes exactly, respectively. Each reaction mixture is treated with eserine solution (0.1 ml) and is left at room temperature, after which the mixture is allowed to stand in a water bath (20° C.) until the solution in the test tube is cooled to 30°±2° C. (in about 10 minutes). After this, OD at 570 nm is measured with reference to water. The pH Blank and pH Serum are determined in accordance with the calibration curve previously prepared. The ΔpH (i.e. pH Blank minus pH Serum) values thus-obtained are indicated in the following table.

TABLE 7

| | A | Cholinesterase activity (Δ pH) of acetyl choline chloride | | | |
|---|---|---|---|---|---|
| | B | Cholinesterase activity (Δ pH) of o-methylbenzoyl choline chloride | | | |

| | Substrate | | | Substrate | |
|---|---|---|---|---|---|
| Serum No. | A | B | Serum No. | A | B |
| 1 | 0.83 | 1.30 | 6 | 0.35 | 0.87 |
| 2 | 0.75 | 1.28 | 7 | 0.58 | 1.10 |
| 3 | 1.46 | 1.90 | 8 | 0.43 | 0.90 |
| 4 | 0.65 | 1.20 | 9 | 0.60 | 1.15 |
| 5 | 0.70 | 1.25 | 10 | 0.63 | 1.17 |

This table indicates that the correlation between ΔpH of acetyl choline chloride and ΔpH of o-methylbenzoyl choline chloride is excellent.

| Correlation coefficent | 0.993 |
|---|---|
| Regresson line | y = 0.928 X + 0.564 |

(wherein y represents the value measured by using o-methylbenzoyl choline chloride, the substrate of the present invention and X represents the value measured by using acetyl choline chloride).

Thus it is possible to simply determine the cholinesterase activity with reference to the previously prepared list of correlations between the ΔpH of acetyl choline chloride and the cholinesterase activity (IU).

EXAMPLE 4

The results shown in Table 6 were obtained in a similar manner to that described in Reference 3 with the exception that serum No. 5 used in Reference 3 was repeatedly determined. As is apparent from this table, the use of the substrate of the present invention results in a very small coefficient of variation and exact analytical value.

TABLE 8

| | A | Cholinesterase activity (Δ pH) of acetyl choline chloride | | | |
|---|---|---|---|---|---|
| | B | Cholinesterase activity (Δ pH) of o-methylbenzoyl choline chloride | | | |

| | Substrte | | | Substrate | |
|---|---|---|---|---|---|
| Serum No. | A | B | Serum No. | A | B |
| 1 | 0.68 | 1.24 | 6 | 0.70 | 1.25 |
| 2 | 0.73 | 1.26 | 7 | 0.74 | 1.25 |
| 3 | 0.69 | 1.25 | 8 | 0.69 | 1.26 |
| 4 | 0.70 | 1.25 | 9 | 0.76 | 1.25 |
| 5 | 0.65 | 1.23 | 10 | 0.68 | 1.24 |

| Substrate used | A | B |
|---|---|---|
| Mean value | 0.696 | 1.247 |
| Standard deviation | 0.025 | 0.009 |
| Coefficient of variation (%) | 3.59 | 0.72 |

EXAMPLE 5

Preparation of the compounds (substrates) of the present invention (A) Synthesis of o-methylbenzoyl choline chloride:

o-benzoyl chloride (25 g) and choline hydrochloride (22.4 g) are heated under reflux to 120°-140° C. for 4 hours, and the reaction solution is concentrated to dryness. The solid is washed well by the addition of n-hexane (100 ml). After the removal of n-hexane by filtration, the material is added to tert-butanol (40 ml) and heated in order to dissolve it. The solution is allowed to stand in a refrigerator at 5° C. overnight to form crystals. The crystals are collected by filtration and recrystallized from a mixture of tert-butanol/ethanol (30 ml; 3:1 by volume), followed by drying under reduced pressure. 33 g of the desired product is obtained in a yield of about 33% (M.P. 142°-143° C.). The desired product is identified by reference to various properties shown in Table 1. In a similar manner to that described above, other substrates are also produced by using corresponding acid chlorides and choline hydrochloride, the properties of which products are also indicated in Table 1.

REFERENCE

Preparation of choline oxidase (A) Determination of the activity:

When choline is oxidized with choline oxidase, hydrogen peroxide is liberated. This hydrogen peroxide is decomposed with peroxidase and transferred to a colour-developing system containing phenol and 4-aminoantipyrine. In detail, a tris buffer solution (0.05 mol/l; pH 7.0) containing 4-aminoantipyrine (0.01 mol/l) and phenol (0.01 mol/l) is treated with peroxidase (500 U/100 ml) to prepare a colour-developing solution. To this solution (3 ml) is added the enzyme solution to be determined (0.1 ml) and a choline chloride solution (1/30 mol/l; 0.1 ml). After carrying out the reaction at 37° C. for 20 minutes, the E.C. (extinction coefficient) at 500 nm is measured. The term "U" (unit of activity) denotes an activity capable of decomposing 1 μmol of the substrate in one minute.

(B) Preparation of choline oxidase:

*Brevibacterium album* KY 4319 (FERM P-3777; NRRL B-11046) is used as the choline oxidase producing microorganism. A seed medium (10 ml) containing choline chloride (2 g/dl), corn steep liquor (0.5 g/dl), yeast extract (0.5 g/dl), sodium glutamate (0.5 g/dl) and magnesium sulfate.7$H_2O$ (0.05 g/dl) is put in a test tube (capacity..70 ml) and sterilized at 120° C. for 15 minutes. After this, one platinum loop of the strain is used to inoculate the medium for culturing at 30° C. for 48 hours with shaking. All broths obtained are transferred to another seed medium (300 ml) containing the same ingredients as those of the first seed medium and put in an Erlenmeyer flask (capacity..2 liter) for culturing at 30° C. for 48 hours with shaking. After completion of the fermentation, all broths are used to inoculate a main medium (3.0 liter) having the same ingredients and put in a 5 liter jar fermentor for culturing at 30° C. for 24 hours with aeration (one liter/liter of the medium/min) and shaking (500 r.p.m.). The fermented liquor contains 0.62 U/ml of choline oxidase.

In order to recover the choline oxidase from the fermented liquor, microbial bodies are separated from the liquor by centrifugation and dispersed in one liter of tris buffer solution (0.05 mol/liter; pH 8.0) which is then transferred to a crusher (Dyno Laboratory mill, KDL type, commercial product of Willy A. Bachofen Inc., Switzerland) to obtain a solution containing crushed microbial bodies. This solution is centrifuged to obtain a supernatant (the above-mentioned amount of choline oxidase produced is determined by using this supernatant as an enzyme solution for measuring the activity of choline oxidase). Ammonium sulfate is added to the supernatant to make it saturated with 30% ammonium sulfate. The precipitates are removed from the saturated solution by centrifugation, and the supernatant thus-obtained is treated with ammonium sulfate to make it saturated with 60% ammonium sulfate. The saturated solution is centriguged to collect the precipitates. The precipitates are dissolved in a tris buffer solution (pH 8.0; 0.05 mol/liter) and subjected to dialysis overnight, by using the same tris buffer solution and a dialysing membrane in the form of tube made of cellophane. The solution in the tube is transferred to a column packed with one liter of DEAE cellulose which has been equilibrated with a tris buffer solution (pH 8.0) containing sodium chloride (0.05 mol/liter). The column is washed with one liter of a tris buffer solution (pH 8.0) containing sodium chloride (0.05 mol/liter), and gradient elution is effected by using an eluting solution containing sodium chloride (0.05-0.45 mol/liter). Fractions containing choline oxidase are collected and combined, and the combined fractions are treated with ammonium sulfate to obtain a solution saturated with 60% ammonium sulfate. The precipitates are collected by centrifugation and dissolved in a tris buffer solution (0.05 mol/liter; pH 8.0). The solution is transferred to 500 ml of Sephadex G-150 (a molecular sieve composed of dexstran derivatives, commercial product of Pharmacia Fine Chemicals Inc., U.S.A.) which has been equilibrated with a tris buffer solution (0.05 mol/liter; pH 8.0), and elution is effected by using an identical buffer solution.

Fractions containing choline oxidase are collected and combined. The combined fractions are made saturated with 60% ammonium sulfate. The precipitates are collected by centrifugation and dissolved in a tris buffer solution (0.05 mol/liter; pH 8.0). The solution is subjected to dialysis overnight, by using the same buffer solution and a dialysing membrane in the form of tube made of cellophane. The dialysed solution is transferred to 500 ml of Sephadex A-50 (weakly basic anion exchange resin, commercial product of Phamacia Fine Chemicals Inc., U.S.A.) which has been equilibrated with a tris buffer solution (0.05 mol/liter; pH 8.0) containing sodium chloride (0.1 mol/liter), and is washed with 500 ml of a tris buffer solution (0.05 mol/liter; pH 8.0) containing sodium chloride (0.1 mol/liter). Then gradient elution is effected by using an eluting solution containing sodium chloride (0.1-0.5 mol/liter). Fractions containing choline oxidase are collected and combined. The combined fractions are subjected to dialysis using a tris buffer solution (0.05 mol/liter; pH 8.0) and a tube made of cellophane. The dialysed solution is freeze-dried to obtain choline oxidase with a yield of about 10% (activity ... 2.2 U/mg of protein).

We claim:

1. A method of determining cholinesterase activity which comprises reacting the cholinesterase with a compound of the formula:

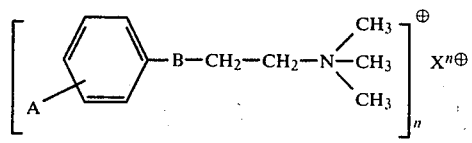

(wherein A represents a hydrogen atom or a $C_{1-5}$ alkyl or alkoxy group and B represents a group of the formula —R—COO— (in which —R— represents an alkenyl group with 2 to 6 carbon atoms); or A represents a hydroxy group in either or both o-positions of the benzene ring or a $C_{1-5}$ alkyl group and B represents a group of the formula —COO—; X represents a stabilising anion and n represents the charge on the anion) and determining the cholinesterase activity by means of the choline and/or acid thereby obtained by titrometric or calorimetric techniques.

2. The method of claim 1 wherein X represents a halide ion and n is 1.

3. The method of claim 2 wherein X represents a chloride ion.

4. The method of claim 1 wherein A represents a hydrogen atom or a methyl or methoxy group in the p-position of the benzene ring and B represents a group of the formula —R—COO— (wherein R represents an alkenyl group with 2 to 6 carbon atoms) or A represents a methyl group in either or both o-positions of the benzene ring and B represents the group —COO—.

5. The method of claim 4 wherein the compound of the formula I is p-methylcinnamoyl choline chloride.

6. The method of claim 4 wherein the compound of the formula I is p-methoxycinnamoyl choline chloride.

7. The method of claim 4 wherein the compound of the formula I is o-methylbenzoyl choline chloride.

8. The method of claim 4 wherein the compound of the formula I is cinnamoylcholine chloride.

9. The method of claim 4 wherein the compound of the formula I is m-methylbenzoyl choline chloride.

10. The method of claim 4 wherein the compound of the formula I is o-hydroxybenzoyl choline chloride.

11. A compound of the formula:

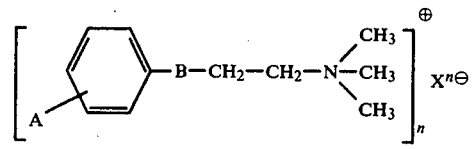

wherein A represents a hydrogen atom or a methyl or methoxy group in the p-position of the benzene ring and B represents a group of the formula —R—COO— (wherein —R— represents an alkenyl group with 2 to 6 carbon atoms); or A represents a methyl group in either or both o-positions of the benzene ring and B represents a group of the formula —COO—; X represents a stabilising anion and n represents the charge on the ion.

12. The compound of claim 11 wherein X represents a halide ion and n is 1.

13. The compound of claim 12 wherein X represents a chloride ion.

14. p-Methylcinnamoyl choline chloride.
15. p-Methoxycinnamoyl choline chloride.
16. o-Methylbenzoyl choline chloride.
17. Cinnamoyl choline chloride.
18. m-Methylbenzoyl choline chloride.
19. o-Hydroxybenzoyl choline chloride.
20. A reagent for determining cholinesterase activity which comprises in combination a compound of the formula I as defined in claim 1, a colour-developing reagent, choline oxidase and a peroxide.
21. The reagent of claim 20 wherein the colour-developing reagent comprises 4-aminoantipyrine and phenol.

* * * * *